United States Patent [19]

Kung et al.

[11] Patent Number: 5,527,715
[45] Date of Patent: Jun. 18, 1996

[54] METHOD AND KIT FOR PYRIDINOLINE ASSAY

[75] Inventors: Viola T. Kung, Menlo Park; Mary J. Cerelli, Burlingame; Yuri Daniloff, Mountain View; Robert F. Zuk, Burlingame, all of Calif.

[73] Assignee: Metra Biosystems, Inc., Mountain View, Calif.

[21] Appl. No.: 208,871

[22] Filed: Mar. 10, 1994

Related U.S. Application Data

[63] Continuation-in-part of Ser. No. 922,906, Jul. 31, 1992, abandoned.

[51] Int. Cl.[6] .................................................. G01N 33/53
[52] U.S. Cl. .......................... 436/547; 435/7.1; 435/7.9; 435/7.92; 435/7.93; 435/7.94; 435/962; 436/86; 436/518; 436/531; 530/387.9; 530/389.1; 530/391.1; 530/391.3
[58] Field of Search .............................. 436/86, 518, 531, 436/547, 548; 435/7.1, 7.9, 7.92, 7.93, 7.94, 975, 962; 530/387.9, 389.1, 391.1, 391.3

[56] References Cited

U.S. PATENT DOCUMENTS 5,004,806  4/1991  Kung ........................................ 530/415

FOREIGN PATENT DOCUMENTS 9110141  7/1991  WIPO .

*Primary Examiner*—Toni R. Scheiner
*Assistant Examiner*—Susan C. Wolski
*Attorney, Agent, or Firm*—Vincent M. Powers; Peter J. Dehlinger

[57]  ABSTRACT

A method of assaying a human urine sample, by measuring a concentration of pyridinium crosslinks from which the concentration of total hydrolysed pyridinoline in the sample can be determined, is disclosed. In the method, a urine sample is reacted with an anti-Pyd antibody reagent which preferably has a ratio of reactivity toward native free pyridinoline and urinary pyridinoline peptides larger than 1,000 daltons in molecular weight, of greater than 10:1. By measuring the extent of immunocomplex formed by the reaction, the concentration of total hydrolysed pyridinoline in the sample can be calculated. Also disclosed are an antibody reagent and kit which can be used in the method.

5 Claims, 4 Drawing Sheets

METHOD AND KIT FOR PYRIDINOLINE ASSAY

This application is a continuation-in-part of U.S. patent application Ser. No. 07/922,906 filed Jul. 31, 1992, now abandoned.

FIELD OF THE INVENTION

The present invention relates to a method for determining pyridinoline crosslink levels in human urine sample and to an antibody reagent and kit for use in the method.

References

Black, D., et al., *Anal. Biochem.* 169:197–203 (1988).
Black, D., et al., *Annals of Rheumatic Diseases* 48:641–644 (1989).
Campbell, A., Monoclonal Antibody and Immunosensor Technology, Elsevier (1991).
Cook, J., et al., *Ann. Clin. Biochem.* 12:219 (1975).
Daniloff, Y., et al., *Connect. Tissue. Res.* 27:187 (1992).
Eyre, D. R., et al., *Anal. Biochem.* 13.7:380–388 (1984).
Eyre, D. R., et al., *FEBS* 2:337–341 (1987).
Fujimoto, D., et al., *J. Biochem.* 83:863–867 (1978).
Fujimoto, D., et al., *J. Biochem.* 9:4:167–173 (1983).
Gosling, J., Clin. Chem. 36(8):1408 (1990).
Gunja-Smith, Z., et al., *Biochem. J.* 197: 759–762 (1981).
Harlow, E., et al., Antibodies: A Laboratory Manual, Cold Spring Harbor Lab (1988).
Henkel, W., et al., *Eur. J. Biochem.* 165:427–436 (1987).
Macek, J., et al., *Z. Rheumatol.* 46:237–240 (1987).
Ogawa, T., et al., *Biochem. Biophys. Res. Commune.* 107:1251–1257 (1982).
Robins, S. P., Biochem J. 207:617–620 (1982a).
Robins, S. P., in "Collagen in Health and Disease" (Weiss, J. B., et al., eds.) pp. 160–178, Churchill Livingstone, Edinburgh (1982b).
Robins, S. P., *Biochem. J.* 215:167–173 (1983).
Robins, S. P., et al., *Ann Rheumatic Dis,* 45: 969–973 (1986).
Robins, S. P., et al., *Biochim. Biophys. Acta.* 914:233–239 (1987).
Segel, I., Biochemical Calculations, John Wiley and Sons, (1976).
Seibel, et al., *J. Rheumatol* 16:964–970 (1989).
Wong, S. S., Chemistry of Protein Conjugation and Cross-Linking, CRC Press, Boca Raton, Florida (1991).

Background of the Invention

There are a variety of conditions in humans which are characterized by a high level of bone resorption and by an abnormal balance between bone formation and bone resorption. Among the more common of these are osteoporosis, Paget's disease, and conditions related to the progress of benign and malignant tumors of the bone and metastatic cancers which have been transferred to bone cells from, for example, prostate or breast initial tumors. Other conditions which are associated with changes in collagen metabolism include osteomalacial diseases, rickets, abnormal growth in children, renal osteodystrophy, and a drug-induced osteopenia. Irregularities in bone metabolism are often side effects of thyroid treatments and thyroid conditions per se, such as primary hypothyroidism and thyrotoxicosis as well as Cushing's disease.

It has been recognized that disorders of bone resorption or other conditions characterized by an abnormal balance between bone formation and bone resorption can be detected by altered levels of pyridinium crosslinks in urine (Robins, 1982b; Macek; Black). The crosslinks take the form of compounds containing a central 3-hydroxy pyridinium ring in which the ring nitrogen is derived from the epsilon amino group of lysine or hydroxylysine (Fujimoto, 1978; Robins, 1982a; Gunja-Smith; Ogawa; Eyre).

The pyridinium crosslink compounds found in urine can be grouped into four general classes: (1) free, native crosslinks having a molecular weight of about 400 daltons (Fujimoto), (2) glycosylated crosslinks and crosslink peptide forms having a molecular weight of between about 550 and 1,000 daltons (Robins, 1983), (3) crosslink peptide forms having a molecular weight between 1,000 and 3,500 daltons (Robins, 1983, 1984, 1987; Henkel; Eyre), and (4) crosslink peptide forms having a molecular weight greater than 3,500 daltons. In normal adults, these forms account for about 38% (1), 40% (2), 15% (3), and 7% (4) of total urinary crosslinks (Daniloff). About 80% of the free crosslinks in normal adults is pyridinoline (or Pyd), derived from a hydroxylysine residue, and about 20%, deoxypyridinoline, or Dpd, derived from a lysine residue, and this ratio of Pyd/Dpd applies roughly to the other three classes of crosslinks in urine. The higher molecular weight crosslinks can be converted to free crosslinks by acid hydrolysis (Fujimoto, 1978).

Methods for measuring pyridinium crosslinks in urine have been proposed. One of these methods involves the measurement of total hydrolysed Pyd, i.e., Pyd produced by extensive hydrolysis of urinary crosslinks, by quantitating the hydrolysed Pyd peak separated by HPLC (Fujimoto, 1983). The relationship between total hydrolysed Pyd to age was determined by these workers as a ratio to total hydrolysed Pyd/creatinine, where creatinine level is used to normalize crosslink levels to urine concentration and skeletal mass. It was found that this ratio is high in the urine of children, and relatively constant throughout adulthood, increasing slightly in old age. The authors speculate that this may correspond to the loss of bone mass observed in old age.

Studies on the elevated levels of total crosslinks in hydrolyzed urine of patients with rheumatoid arthritis has been suggested as a method to diagnose this disease (Black). The levels of total hydrolyzed crosslinks for patients with rheumatoid arthritis (expressed as a ratio of total crosslinks measured by HPLC to creatinine) were elevated by a factor of 5 as compared to controls. However, only total hydrolysed Pyd, but not total hydrolysed Dpd, showed a measurable increase.

In a more extensive study using hydrolyzed urines, Seibel et al. showed significant increases in the excretion of total hydrolysed Pyd crosslinks relative to controls in both rheumatoid and osteoarthritis, but the most marked increases for total hydrolysed Pyd were in patients with rheumatoid arthritis (Seibel).

Assay methods, such as those just noted, which involve HPLC quantitation of crosslinks from hydrolysed samples, or crosslink subfractions from non-hydrolysed samples, are relatively time-consuming and expensive to carry out, and may not be practical for widespread screening or monitoring therapy in bone-metabolism disorders.

Immunoassays have also been proposed for measuring urinary crosslinks. U.S. Pat. No. 4,973,666 discloses an assay for measuring bone resorption by detection in urine of specific pyridinium crosslinks, characterized by specific peptide extensions, associated with bone collagen. Two specific entities having peptide extensions presumed to be associated with bone collagen are described. These are obtained from the urine of patients suffering from Paget's disease, a disease known to involve high rates of bone formation and destruction. The assay relies on immunospecific binding of crosslink compounds containing the specific peptide fragment or extension with an antibody prepared against the crosslink peptide. It is not clear whether and how the concentration of crosslink peptide being assayed relates to total urinary crosslinks.

Robins has described a technique for measuring pyridinoline in urine by the use of an antibody specific to hydrolysed Pyd (Robins, 1986). The method has the limitation that the antibody was found to be specific for the hydrolyzed form of Pyd, requiring that the urine sample being tested first be treated under hydrolytic conditions. The hydrolytic treatment increases the time and expense of the assay, and precludes measurements on other native pyridinium crosslinks.

Ideally, an assay method for measuring bone collagen metabolism, according to crosslink levels in the urine, should (a) employ a non-hydrolysed urine (or serum) sample, to avoid the need for initial sample treatment by acid hydrolysis, (b) utilize an antibody reagent to detect one or more pyridinoline components, to reduce the time and expense of analysis over conventional HPLC tests, and (c) provide a quantitative measure of crosslinks or Pyd which is related to total crosslinks or total Pyd levels in the sample.

SUMMARY OF THE INVENTION

The present invention includes a method of assaying bone collagen degradation levels in a human subject. In the method, a urine sample from a human subject is reacted with an antibody reagent which has a ratio of reactivity toward native Pyd (N-Pyd) and urinary pyridinoline-peptide (Pyd-peptide) larger than 1,000 daltons in molecular weight, of greater than 10:1. According to one aspect of the invention, the amount of pyridinium crosslink measured in the urine sample correlates directly with, and can be used to determine, the concentration of total Pyd in the sample.

The urine sample may be passed through a nitro-cellulose filter, or otherwise contacted with a nitrocellulose surface, to improve assay performance.

The antibody reagent employed in the method has a preferred binding constant, measured with respect to NPyd, of greater than $1 \times 10^7$/molar, and a ratio of reactivity toward N-Pyd and urinary Pyd-peptides larger than 1,000 daltons in molecular weight, of greater than 25:1.

In one general embodiment, the antibody reagent includes a polyclonal antibody produced by an animal immunized with Pyd. The concentration of pyridinium crosslinks measured in the assay is related to the concentration of total Pyd in the sample, as measured by HPLC of hydrolysed Pyd, by a linear relationship.

In another general embodiment, the antibody reagent is a monoclonal antibody produced by immortalized lymphocytes obtained from an animal immunized with free pyridinoline, such as the antibody produced by the cell line identified by ATCC No. HB11089. The concentration of crosslinks measured in the assay is related to the concentration of total Pyd in the sample, as measured by HPLC of hydrolysed Pyd, by a linear relationship with a slope of about 0.3–0.5.

In a related aspect, the invention includes a method of determining a concentration of pyridinoline crosslinks in a non-hydrolyzed urine sample, that correlates with the concentration of pyridinoline crosslinks measurable after hydrolysis of the sample, with an R value of greater than 0.85. In the method, a non-hydrolysed urine sample from a human subject is reacted with a polyclonal antibody reagent produced by immunizing an animal with hydrolyzed pyridinoline conjugated to a carrier. The reaction conditions are effective to form an immunocomplex between pyridinoline crosslinks in the urine sample and the antibody reagent. Detection of the amount of immunocomplex formed provides a measure of the concentration of total pyridinoline crosslinks in the sample.

In another aspect, the invention includes an antibody reagent which is immunoreactive with N-Pyd in urine, and which is characterized by a ratio of reactivity toward N-Pyd and urinary Pyd-peptides larger than 1,000 daltons in molecular weight, of greater than 10:1, and preferably greater than 25:1.

The reagent may include the polyclonal or monoclonal antibodies described above, such as the monoclonal antibody produced by the cell line identified by ATCC No. HB11089.

Also forming part of the invention is a diagnostic kit for use in assaying bone degradation levels in humans. The kit includes an antibody reagent which has a ratio of reactivity toward N-Pyd and urinary Pyd-peptides larger than 1,000 daltons in molecular weight, of greater than 10:1; and detection reagent(s) for detecting the amount of immunocomplex formed by reaction of the antibody reagent with pyridinium crosslinks.

In one general embodiment, the kit may include a solid-phase support having a surface-attached binding agent which may be either the antibody reagent or Pyd capable of competing with N-Pyd in a sample for binding to the antibody reagent.

These and other objects and features of the invention will become more fully apparent when the following detailed description of the invention is read in conjunction with the accompanying drawings.

DETAILED DESCRIPTION OF THE INVENTION

I. Definitions

Figure 1A:
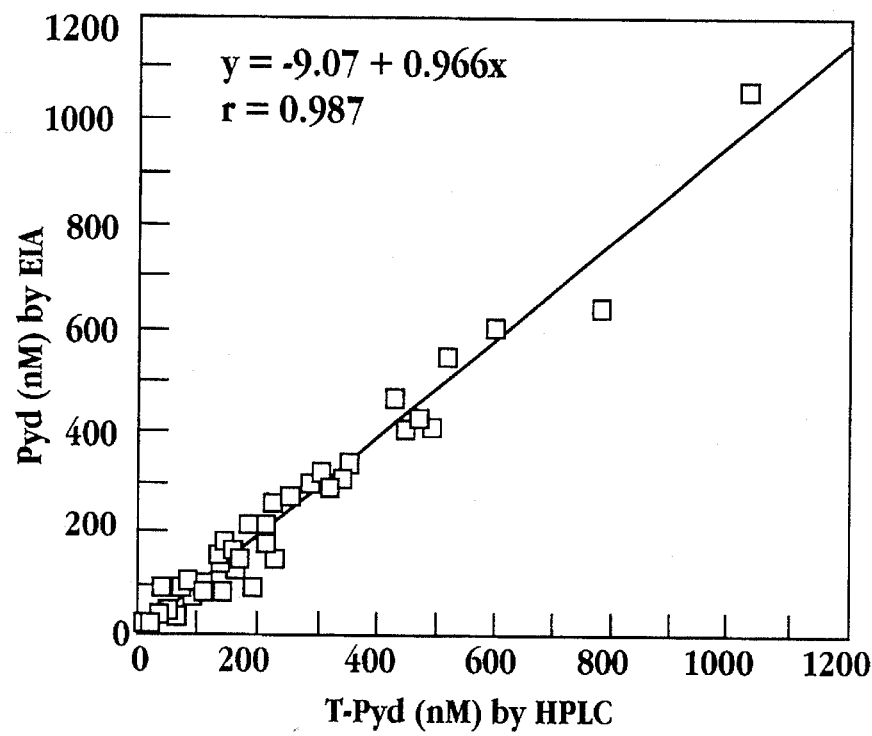
FIGS. 1A and 1B show linear regression plots of native pyridinium crosslink concentrations measured using a polyclonal antibody reagent designated I-3 (FIG. 1A) or a polyclonal antibody reagent designated VI-8 (FIG. 1B), versus total hydrolysed pyridinoline measured by HPLC.

As used herein, the terms below have the following definitions:

"Pyd" or "pyridinoline" or "free pyridinoline" refers to the crosslink compound shown at I below, where the ring N is derived from the ε amino group of a hydroxylysyl residue, and "Dpd" or "deoxypyridinoline" or "free deoxypyridinoline" refers to the crosslink compound shown at II below, where the ring N is derived from the ε amino group of a lysyl residue.

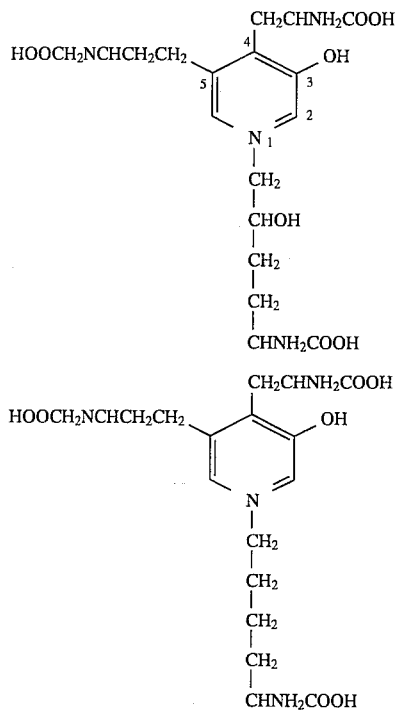

"Free crosslinks" refers to either compounds I or II or a mixture of the two.

"Glycosylated pyridinoline" or "glyco-Pyd" refers to glycosylated forms of compound I. Two glyco-Pyd crosslinks which have been identified are Gal-Pyd, having the acetal structure shown at III, and Glc-Gal-Pyd, having the acetal structure shown at IV:

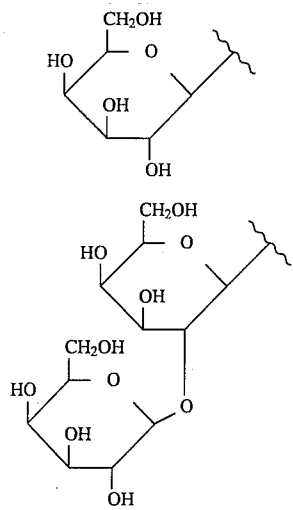

"Pyd-peptides" or "pyridinoline-peptides" refers to peptide-derivatized forms of compound I, in which one or more of the three amino acid residues in the compound is linked via a peptide linkage to additional amino acid residues.

"Pyd-peptides having a molecular weight greater than 1000 daltons" or "Pyd-peptides (MW>1000)" refers to Pyd-peptides retained by a dialysis membrane having a 1,000 molecular weight cutoff.

Pyd-peptides having a molecular weight greater than 3500 daltons" or "Pyd-peptides (MW>3500) refers to a Pyd-peptides retained by a dialysis membrane having a 3,500 molecular weight cutoff.

"Pyd crosslinks" refers to the pyridinium crosslinks in urine which contain compound I either in free or derivatized form. Pyd crosslinks include Pyd, glyco-Pyd and Pyd-peptides. Similarly, "Dpd crosslinks" refers to the pyridinium crosslinks in urine which contain compound II either in free or derivatized form.

"Total H-Pyd" refers to total hydrolysed Pyd produced by hydrolyzing Pyd crosslinks to Pyd. Similarly, "total H-Dpd" refers to total hydrolysed Dpd produced by hydrolyzing Dpd crosslinks to Dpd.

"Hydrolysed-Pyd" or "H-Pyd" refers to Pyd produced by hydrolysing Pyd crosslinks in 6N HCl at 110° C. for 16 hours. Similarly, "Hydrolysed-Dpd" or "H-Dpd" refers to Dpd produced by hydrolysing Dpd crosslinks in 6N HCl at 110° C. for 16 hours.

"Native Pyd" or "N-Pyd" refers to Pyd obtained from urine which has not been subjected to hydrolytic conditions. Similarly, "Native Dpd" or "N-Dpd" refers to Dpd obtained from urine which has not being subjected to hydrolytic conditions.

"Pyridinium crosslinks" refers to pyridinium crosslinks which contain compounds I and/or II in free and/or derivatized form.

II. Preparation of Anti-Pyd Antibody Reagent

This section describes the production of polyclonal and monoclonal antibodies, or antibody reagent, which has selectivity for N-Pyd. In a preferred embodiment, the antibody has a ratio of reactivity toward N-Pyd and urinary pyridinoline-peptide larger than 1,000 daltons in molecular weight, or Pyd-peptides (MW>1000), of greater than 10:1.

A. Immunogen

The immunogen used in producing the antibody reagent is Pyd conjugated to a carrier molecule, typically a carrier protein such as keyhole limpet hemocyanin or a serum albumin.

Gross separation of the pyridinium crosslinks to purify Pyd from other pyridinium compounds in urine can be achieved, by fractionation of urine, as described in Examples 1 and 2. Briefly, a concentrate of urine is applied to a Sephadex G-10 column and the total pyridinium-containing fractions are eluted. The eluate is then applied to a column of phosphocellulose equilibrated with sodium citrate, and eluted with salt. This procedure results in the "free" crosslinks as a single peak. As the sample is not subjected to hydrolysis conditions, this peak contains not only the N-Dpd and N-Pyd forms, but also glyco-Pyd, including Gal-Pyd and Glc Gal-Pyd as described above. Further separation of this native free crosslink fraction is then conveniently conducted by standard methods, for example, using ion exchange on sulfonated polystyrene beads as described above, or using HPLC. Typical protocols for this separation are found, for example, in Black, et al.; and Seibel, et al. and detailed in Example 2.

Alternatively, the Pyd may be H-Pyd produced by acid hydrolysis of pyridinium crosslinks in bone collagen or urine, and subsequent purification of total H-Pyd, as described in Example 1.

Coupling of Pyd to a carrier protein is by standard coupling methods, typically using a bifunctional coupling agent which forms, at one coupling end, an amide linkage to one of the free carboxyl groups of Pyd, and at the other coupling end an amide or ester or disulfide linkage to the carrier protein, according to standard methods. Alternatively, Pyd can be directly coupled to the protein, e.g., in the presence of a carboxyl activating agent such as EDC (1-(3-dimethylaminopropyl)-3-ethylcarbodiimide), also according to well known methods. The latter approach is illustrated in Examples 3A and 3B, which describe the coupling of Pyd to bovine serum albumin (BSA) and keyhole limpet hemocyanin (KLH), respectively, by EDC activation. General coupling reactions for derivatizing a carrier protein with a peptide antigen are given in Harlow, pp. 77–87, and Wong, 1991.

B. Polyclonal Antibody Reagent

Polyclonal antibody preparation is by conventional techniques, including injection of the immunogen into suitable mammalian subjects, such as rabbits or mice, according to immunological protocols generally known in the art, e.g., Harlow, pp. 93–115. Typically, rabbits are injected subcutaneously with the immunogen in an adjuvant, and booster immunizations are given by subcutaneous or intramuscular injection every 2–3 weeks; mice may be injected intraperitoneally according to a similar schedule. Blood is collected at intervals, e.g. 1–2 weeks after each immunization injection. Antisera may be titrated to determine antibody formation with respect to N-Pyd, according to standard immunoprecipitation methods (Harlow, pp. 423–470). Details of one method for producing polyclonal antibodies are given in Example 3.

Where the immunogen used is H-Pyd, rather than N-Pyd, antisera obtained from some immunized animals may not be strongly reactive with N-Pyd, as, for example, was reported in PCT Publication No. WO 91/10141. However, antisera which show high binding selectivity for N-Pyd, as defined herein, have been produced in animals immunized with H-Pyd immunogens, as detailed in Example 3.

The relative binding specificity of the antibody reagent for N-Pyd and other pyridinium crosslinks can be determined by the competitive binding assay for N-Pyd described in Section IV below. Briefly, various purified crosslink samples, including purified N-Pyd, are reacted with a limiting amount of the polyclonal antibody reagent over a solid-phase support having attached N-Pyd, as detailed in Example 6, under conditions in which the sample pyridinium crosslinks compete with the support-bound N-Pyd for binding to the antibody. The extent of binding of antibody to the solid-support provides a measure of the relative affinities of N-Pyd and the sample crosslink for the antibody reagent.

In the method described in Example 6, the levels of binding of N-Pyd, N-Dpd, glyco-Pyd (optional), Pyd-peptides (MW>1,000), Pyd-peptides (MW>3500) (optional), and a mixture of amino acids (optional), to polyclonal antisera from designated I-3 and VI-8 (Example 3C) were examined.

The apparent N-Pyd concentration of each sample was determined using a standard curve established using purified N-Pyd. The percent reactivity of each sample was calculated as a ratio of apparent concentration (measured using the N-Pyd standard curve above) to total Pyd crosslink concentration in the sample determined by HPLC for total H-Pyd (times 100), or total H-Dpd in the case of the N-Dpd sample. The results for the I-3 polyclonal antibodies are shown in Table 1, where reactivity with N-Pyd has been defined as 100%.

TABLE 1

| Cross-Reactivity of Polyclonal Antiserum I-3 | |
| --- | --- |
| N-Pyd | 100% |
| N-Dpd | 53% |
| Glyco-Pyd | 11% |
| Pyd-Peptide (>1000) | <2% |
| Pyd-Peptide (>3500) | <2% |

As seen, the antibody reagent is relatively specific for N-Pyd, showing reduced reactivity with N-Dpd, still less reactivity for glyco-Pyd and only poor reactivity with larger peptide forms of Pyd. In accordance with one aspect of the invention, the antibody reagent has a reactivity toward native pyridinoline (N-Pyd) and urinary pyridinoline-peptide larger than 1,000 daltons in molecular weight, i.e., Pyd-peptides (MW>1000), of greater than 10:1, and preferably greater than 25:1, as measured by the above antigen-competition assay. In the polyclonal reagent tested, this ratio is greater than 50:1.

Binding properties of a second polyclonal antibody reagent (designated VI-8) obtained by the procedure of Example 3 are shown in Table 2 below.

TABLE 2

| Cross-Reactivity of Polyclonal Antiserum I-3 | |
| --- | --- |
| N-Pyd | 100% |
| N-Dpd | <10% |
| Pyd-Peptide (MW>1000) | <5% |
| Amino Acid Mixture | ~12% |

As seen, the antibody reagent is specific for N-Pyd, showing less than 10% cross-reactivity with N-Dpd, less than 5% cross-reactivity with Pyd-peptides (MW>1000), and moderate (~12%) cross-reactivity with the amino acid mixture.

The antibody reagent preferably has a binding affinity constant for N-Pyd of greater than about $1\times10^7$/molar, and more preferably greater than about $5\times10^7$/molar. The binding constant for polyclonal antisera can be determined by known methods (e.g., by Scatchard analysis using an immunoprecipitation or ELISA assay; see Campbell, Segel), and represents an average binding affinity constant value for the antibodies in the antisera which are specific against N-Pyd. The polyclonal antibodies designated I-3 and VI-8 noted above were found to have binding constants for N-Pyd of $1\times10^7$ and $1\times10^8$/molar, respectively, as determined by Scatchard analysis.

C. Monoclonal Antibody Reagent

To prepare a monoclonal antibody reagent, the Pyd immunogen described above is used to immunize an animal, such as a mouse, from which antigen-specific lymphocytes can be obtained for immortalization. These methods were used to generate a hybridoma cell line which has a high specificity toward N-Pyd. The cell line has been deposited with the American Type Culture Collection, 12301 Parklawn Drive, Rockville, Md. 20852, and has been assigned ATCC No. HB11089.

Briefly, in producing the cell line, mice were immunized by intraperitoneal injection of the H-Pyd-KLH immunogen similar to that described in Example 3. 8 weeks after initial immunization, spleen cells were harvested, and fused with a P-3X63 Ag8.653 myeloma cell line. Selection for successful fusion products was in HAT medium, according to published methods (see, generally, Harlow, pp. 196–212). Successful fusion products were then screened for immunoreactivity with N-Pyd, by antigen capture in solution by immunoprecipitation. Several cell lines which showed high affinity binding to N-Pyd were subcloned by limiting dilution and further screened for production of antibodies with high binding affinity for N-Pyd. One of the subcloned cell lines which gave high antibody affinity for N-Pyd is the cell line identified by ATCC No. HB11089.

To produce the antibody reagent, the hybridoma cell line is grown in a suitable medium, such Dulbecco's modified Eagle's medium (DME) (Harlow, pp. 247–270). Mabs are harvested from the medium and can be concentrated and stored according to published methods (Harlow pp. 271–318).

The monoclonal antibody reagent prepared from hybridoma cell line ATCC HB11089 has a measured affinity constant, with respect to N-Pyd, of about $9.7 \times 10^6$/molar. The affinity constant was measured by Scatchard analysis using an immunoprecipitation assay (Campbell, Segel).

As noted above, an important feature of the present invention is the specificity of the antibody reagent for N-Pyd, relative to larger molecular weight pyridinium crosslinks in urine. The Mab antibody reagent produced by cell line ATCC HB11089 was examined for reactivity toward N-Pyd, N-Dpd, and Pyd-peptides (MW>1000) and (MW>3500), according to the antigen competition described above and detailed, for the Mab reagent, in Example 8. The results are shown in Table 3, where as in Table 1, the measured percent reactivities were expressed as ratio (times 100) of pyridinium crosslink concentration determined in the immunoassay, from a standard N-Pyd curve, and total H-Pyd in the sample determined by HPLC.

TABLE 3

Cross-Reactivity of N-Pyd Monoclonal Antibody

| | |
|---|---|
| N-Pyd | 100% |
| N-Dpd | 16% |
| Pyd-Peptide (>1000) | 0% |
| Pyd-Peptide (>3500) | 1% |

As seen, compared with the reactivity with N-Pyd, the Mab antibody reagent shows substantially lower reactivity toward N-Dpd than the polyclonal reagent, and little or no reactivity toward Pyd-peptides isolated from urine. As above, the Mab reagent has a reactivity toward native pyridinoline (N-Pyd) and Pyd-peptides (MW>1000), of greater than 10:1, preferably greater than 25:1, and in the present case, higher than 100:1, as measured by the above antigen-competition assay.

III. Immunoassay Kit

In another aspect, the invention includes a diagnostic kit for use in assaying bone collagen degradation levels in a human subject. The kit includes an antibody reagent of the type described in the section above, characterized by a ratio of reactivity toward N-Pyd and Pyd-peptides (MW>1000) of greater than 10:1; and a reporter-labeled detection reagent, or means, for detecting the amount of immunocomplex formed by reaction of the antibody reagent with pyridinium crosslinks in a fluid sample, such as a urine sample, from the human subject.

Figure 3A:
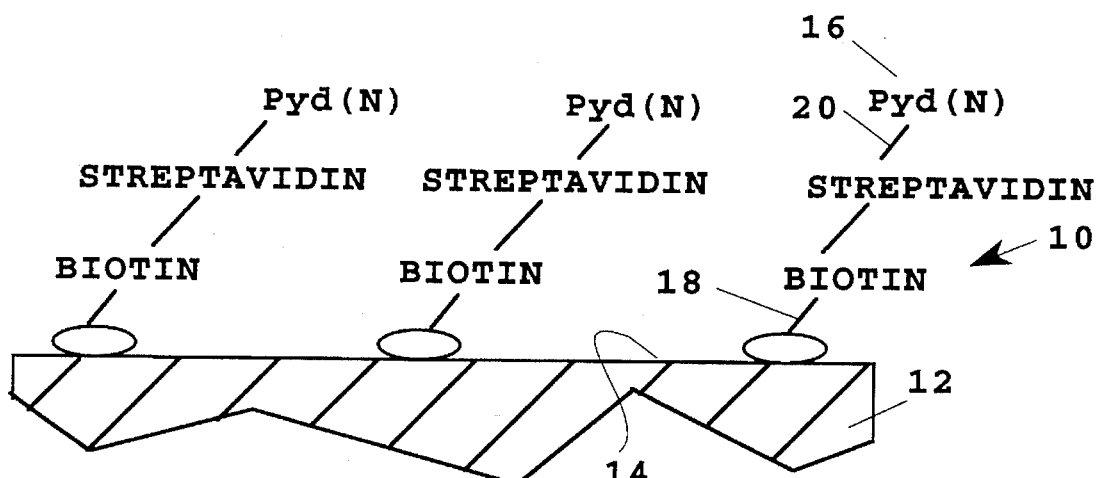
FIG. 3A–3C illustrate steps in practicing a method of the invention, using one embodiment of an assay kit according to the invention.

In one general embodiment, the kit includes a solid-phase support having surface attached binding molecules effective to bind a reporter group in the detection reagent in proportion to the amount of pyridinium crosslinks in the sample which are immunoreactive with the antibody reagent. One specific embodiment of such a kit is shown at 10 in FIGS. 3A–3C. A solid-phase support 12 in the kit a surface to which the binding agent can be adsorbed or chemically attached. A variety of glass and polymer resin supports having chemically derivatizable groups, or surfaces effective in protein adsorption are available. In one preferred embodiment, the kit provides 96 assay wells in a microtitre plate, where the well surfaces form the solid-phase support surfaces in the kit.

The binding agent in kit 10 is N-Pyd, indicated by Pyd(N) molecules in the figures, such as at 16. The binding agent is attached to the solid phase—in this case each of the wells in a 96-well microtitre plate—by first adsorbing an ovalbumin-biotin complex, such as complex 18 in FIG. 3A, to the well surfaces, then attaching an N-Pyd-streptavidin complex, such as complex 20 in FIG. 3A, to the adsorbed biotin. Methods for forming an N-Pyd coated microtitre plate is detailed in Example 4.

Figure 3B:
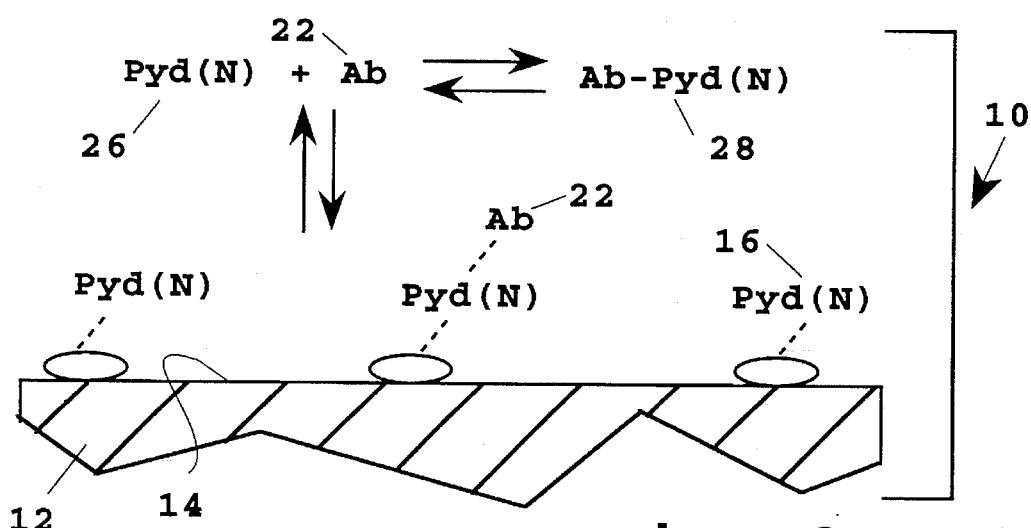
Figure 3C:
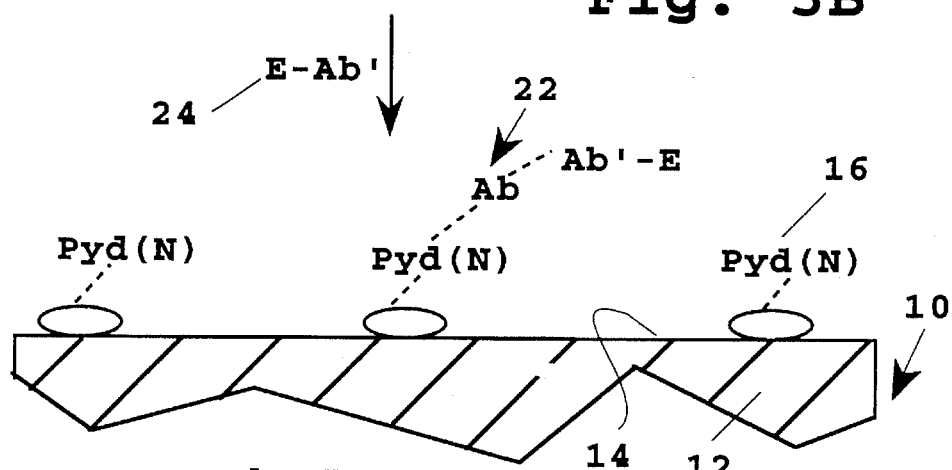

The antibody reagent in the kit is indicated at 22 in FIGS. 3B and 3C, and includes the polyclonal or monoclonal reagent described in the section above. As shown in FIG. 3B, pyridinium crosslinks in a sample, such as the N-Pyd crosslink indicated at 26, competes with surface-bound N-Pyd for binding to the antibody reagent. The immunoreaction formed by reaction of the antibody reagent with sample crosslinks is indicated at 28 in this figure.

The detection reagent in the kit is a reporter-labeled second antibody, indicated at 24 in FIG. 3C, which is effective to bind to antibody reagent which is itself bound to N-Pyd attached to the solid support. Reporter-labeled antibodies, such as enzyme-labeled antibodies, are commercially available or readily constructed (Harlow, pp. 319–358) for a variety of reporter moieties. One preferred enzyme in a labeled antibody is alkaline phosphatase which can react with a p-nitrophenylphosphate substrate to produce a colored product having a strong absorption peak at 405 nm.

The antibody in the detection reagent is typically an anti-IgG antibody, such as an anti-rabbit IgG antibody, where the polyclonal antibody reagent in the kit is obtained from immunized rabbits, or an anti-mouse IgG antibody, where the antibody reagent is a mouse monoclonal antibody.

The detection means in the kit may also include necessary substrates or the like needed for detection of the reporter in the reporter-labeled antibody.

In an alternative embodiment of a kit having a solid-phase support, the binding agent attached to the support is the antibody reagent described in Section II. The antibody may be attached to the solid support by a variety of known methods, including chemical derivatization or high-affinity binding of the antibody by support-bound protein A or anti-IgG antibody, according to standard methods.

In another general embodiment, the kit is designed for a homogenous assay in which sample pyridinium crosslinks can be detected directly in solution. The antibody reagent of the invention can be adapted for a variety of homogeneous assay formats, for example based on coupled enzymes, fluorescence quenching, chemiluminescence, or EMIT configuration (Gosling).

IV. Immunoassay Method

The invention provides a method for assaying bone collagen degradation activity in a human subject, by measuring, in a urine sample from the subject, a concentration of native pyridinium crosslinks from which the concentration of total hydrolysed pyridinoline (or NP-yd) in the sample can be determined. The method involves reacting a urine sample from an individual with the antibody reagent described in Section II, forming an immunocomplex between the antibody composition and native pyridinium crosslinks in the sample, and measuring the amount of the immunocomplex formed.

As indicated in Section III above, the reaction of sample with the antibody reagent may be carried out in a solid-phase format, using a variety of configurations, or in a homogeneous assay format. For illustrative purposes, the immunoassay method will be described with particular reference to the assay format involving the solid-phase support format shown in FIG. 3A–3C. It will be appreciated how the method can be adapted to other solid-phase or homogeneous assay formats.

Experiments conducted in support of the present invention, and described in Example 9, indicate that the reliability of the assay method can be improved significantly by contacting the sample with a nitrocellulose filter to remove interfering substances in the sample.

The data in Table 4 illustrate the improvement in pyridinium crosslink levels and reliability when the urine sample is first treated by filtration through a nitrocellulose filter. The table shows measured pyridinium crosslink levels which are measured in six urine samples (lefthand column) without filtration (second column from the left) and with filtration (second column from the right). As seen, the measured concentration of pyridinium crosslinks increased by between about 7–45 percent after removal of interfering substances, suggesting wide variability in the extent of interference among samples. As will be seen below, the assay results obtained with filtered samples, in accordance with the invention, give crosslink concentration values which are highly correlated with total H-Pyd concentrations in the sample, as measured by HPLC methods, indicating that sample variation due to interference substances has been largely eliminated.

Additional studies carried out in support of the invention indicate that the interfering substances, i.e., substances removed by contact with a nitrocellulose surface, promoted non-specific binding of enzyme-labeled antibody to a solid-phase support with several of the urine samples. The amount of non-specific binding observed for filtered samples was uniformly very low. The procedure should be applicable to other EIA assays in which a small molecular weight analyte is being tested.

TABLE 4

Quantitation of PYD

| Urine ID | PYD (nM) before filtration | PYD (nM) after filtration | % Increase |
| --- | --- | --- | --- |
| 2181 | 111 | 205 | 45.8 |
| 2176 | 167 | 201 | 16.9 |
| 2159 | 357 | 592 | 39.7 |
| 2167 | 337 | 365 | 7.7 |
| 2161 | 97 | 137 | 29.1 |
| 2172 | 244 | 362 | 32.6 |

Continuing the description of the assay method, a known volume, typically 10–50 μl, of the filtered sample is added to the N-Pyd-coated solid support, e.g., the wells in a microtitre plate, and sample addition is followed by addition of a known volume, typically 100–200 μ, of antibody reagent, at a known dilution. The mixture on the solid support surface is then incubated, preferably under conditions effective to achieve equilibrium between the antibody binding to sample pyridinium crosslinks and surface-bound Pyd. In the method detailed in Examples 5 and 7, the incubation is overnight at 2°–8° C.

After incubation the solid support is washed several times to remove antibody not specifically bound to the support, and then incubated with a reporter-labeled anti-IgG antibody effective to bind specifically to support-bound antibody. In the method illustrated in Example 5, which involves a rabbit polyclonal antibody reagent, the reporter-labeled antibody is goat anti-rabbit IgG conjugated with alkaline phosphatase. In the method illustrated in Example 7, which involves a mouse monoclonal antibody reagent, the reporter-labeled antibody is goat anti-mouse IgG derivatized with alkaline phosphatase.

After a short incubation time, the support is again washed to remove non-specifically bound material, and the level of enzyme bound to the support is determined by addition of enzyme substrate, with spectrophotometric determination of converted substrate. Details are given in Example 5.

In a typical assay, N-Pyd standards containing increasing concentrations of N-Pyd are added in duplicate to some of the wells, for purposes of generating an N-Pyd concentration standard curve. Up to 40 samples are then added in duplicate to remaining wells, and the wells are then assay as above. The standard curve is used for determining pyridinium crosslink values for the samples in terms of N-Pyd concentrations. The measured pyridinium concentrations are preferably expressed as a ratio of concentration of pyridinium/creatinine, to normalize the samples for variations in urine concentration and body mass. Urine creatinine concentrations can be assayed by standard methods, such as those based on reaction with alkaline picrate (Cook).

Example 5 illustrates a typical reaction procedure for assaying urine pyridinium levels in accordance with the invention, and using the polyclonal antibody reagent described above (I-3) with respect to Table 1. The assay was carried out in two 96 well microtitre plates, with 12 wells in each plate being used for duplicate samples of 6 N-Pyd standards, and 44 wells in each plate being used for 22 duplicate urine samples from post-menopausal women. Details of the assay are given in Example 5. A standard curve for N-Pyd concentrated, generated from the six N-Pyd standards, was used to calculate, for each unknown sample, the concentration (in nM) of sample pyridinium crosslinks which are immunoreactive with the assay antibody.

The data from Table 1 above indicate that the measured pyridinium concentration is due predominantly to N-Pyd in the sample, with a minor contribution from N-Dpd (whose reactivity with the antibody reagent is only about half that of N-Pyd, and whose total concentration in the sample is only about 20% that of N-Pyd) glyco-Pyd, minor amounts of Pyd-peptides (MW>1,000) and perhaps some contribution from Pyd-peptides whose molecular weights are less than 1,000 daltons.

Aliquots of each urine sample were also hydrolysed and the H-Pyd fraction (representing total pyridinium crosslinks with a Pyd nucleus) was quantitated by HPLC analysis.

FIG. 1A shows a scatter plot of pyridinium crosslinks (in nM) measured by immunoassay (I-3 polyclonal antibodies; y axis) versus total H-Pyd measured by HPLC. The line in the plot is the best-fit linear regression equation which correlates immunoassay values as a function of HPLC total Pyd values. The regression equation is $y = -9.0734 + 0.96602x$.

As seen from FIG. 1A, the concentration of pyridinium crosslinks measured using the polyclonal antibody reagent of the invention is related to the concentration of total hydrolysed pyridinoline in the sample by linear relationship with a slope of about 1, and specifically in this set of data, a slope of 0.97. This linear relationship and the high correlation coefficient (R value=0.987) between measured pyridinium concentration and total Pyd allows for accurate determination of total Pyd values in the assay, from the measured pyridinium crosslink concentration.

Figure 1B:
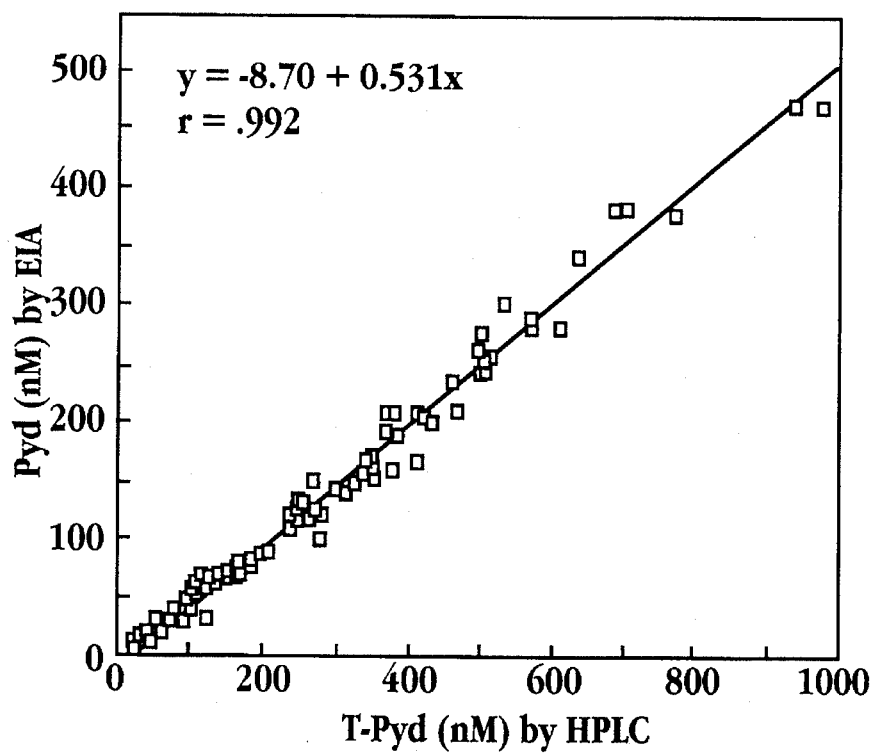

FIG. 1B shows a scatter plot obtained by the same procedures as for FIG. 1A, but using the polyclonal antibodies designated VI-8 (Table 2) instead of the I-3 antibodies. As can be seen from the linear regression equation (y=−8.7035+0.53171x; R value=0.992), the concentration of pyridinium crosslinks measured using this polyclonal antibody reagent is related to the concentration of total hydrolysed pyridinoline in the sample by linear relationship with a slope of about 0.5 and a correlation coefficient (R value) of 0.987. As with the I-3 polyclonal antibodies above, the linear relationship and high correlation coefficient allow for accurate determination of total Pyd values from the measured pyridinium crosslink concentration.

Example 7 illustrates a typical reaction procedure for assaying urine pyridinium levels in accordance with the invention, and using a monoclonal antibody reagent. The assay was carried out in two 96 well microtitre plates, with the 6 standard N-Pyd samples and 44 urine samples employed in the assay above. The concentration (in nM) of sample pyridinium crosslinks was again measured from the N-Pyd standard curve. The data from Table 3 above indicate that the measured pyridinium concentration is due predominantly to N-Pyd in the sample, with only minor contributions from N-Dpd and possibly Pyd-peptides with molecular weights less than 1,000 daltons. This is supported from the data discussed below, which indicates that the monoclonal reagent is immunoreactive with about 40% of the total Pyd-related crosslinks in a urine sample. This is approximately the percentage of N-Pyd present in urine samples.

Figure 2:
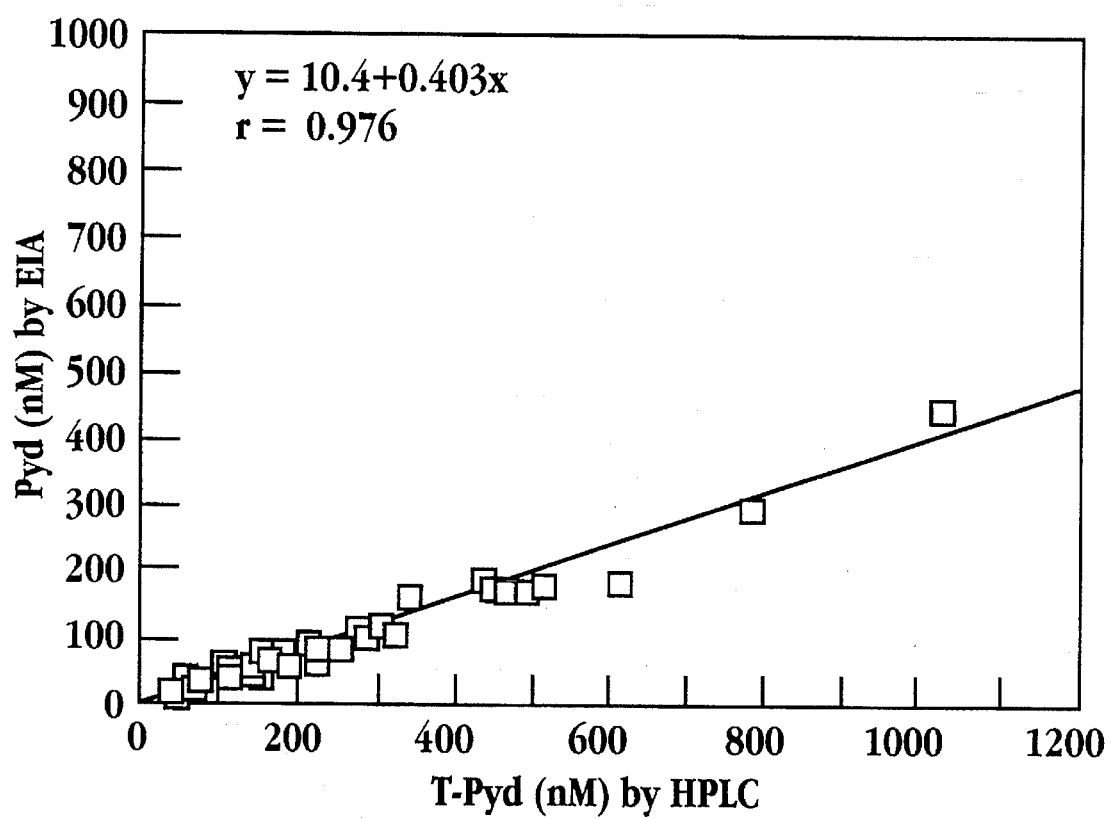
FIG. 2 shows a linear regression plot of native pyridinium crosslink concentrations measured according to the present invention, by immunoassay using a monoclonal antibody reagent, versus total hydrolysed pyridinoline measured by HPLC.

The measured pyridinium crosslink concentrations from the 44 samples were plotted against the total H-Pyd concentrations, measured as above, giving the scatter plot shown in FIG. 2. The best-fit regression line in the figure is given by the equation y=−10.407+0.0.40310x. Thus, the pyridinium crosslink concentration measured in the assay, using a monoclonal antibody reagent is related to the concentration of total hydrolysed pyridinoline in the sample by linear relationship with a slope of between about 0.3–0.5, and specifically in this set of data, a slope of 0.403. As with the polyclonal reagent, the linear relationship between measured pyridinium crosslink concentration and total H-Pyd, and the high correlation (r=0.982) between the two permits for accurate determination of total Pyd values in the assay from the measure pyridinium crosslink levels.

Further, since the assay with the monoclonal reagent provides a good direct measure of N-Pyd, and both polyclonal and monoclonal reagents are strongly correlated, by a linear relationship, with total H-Pyd, it can be appreciated that the pyridinium concentration measured by the polyclonal reagent is related to N-Pyd by a linear relationship (which in the present sample sets, should have a slope of 0.403/0.966=0.417).

It will be appreciated how the pyridinium crosslink concentrations measured in the assay can be used to provide an index to determination of the metabolic status of tissues which generate collagen-derived crosslinks when degradatio.. occurs. As discussed above, a variety of abnormal or pathological bone metabolic conditions are characterized by changes in both N-Pyd and total Pyd in human urine samples. Further, changes in N-Pyd provides a good measure of changes in N-Dpd as well. This latter point is illustrated by the data in Table 5 below, which shows N-Pyd and N-Dpd levels, measured by HPLC from purified N-Pyd and N-Dpd crosslinks in a variety of urine samples.

TABLE 5

| Patient Group | N-Pyd | N-Dpd |
|---|---|---|
| | (nmol/mmol creatinine) | |
| Normal controls | 10.3 ± 1.0 | 3.27 ± 0.57 |
| Osteoporosis | 19.6 ± 2.3 | 5.90 ± 0.68 |
| Paget's Disease | 62.5 ± 11.2 | 19.3 ± 3.83 |
| Hyperparathyroidism | 55.9 ± 14.2 | 16.3 ± 4.81 |
| Rheumatoid arthritis | 38.8 ± 8.36 | 8.92 ± 2.08 |
| Osteoarthritis | 25.8 ± 3.22 | 6.10 ± 0.83 |

These results show dramatically elevated levels of the free crosslinks in patients known to be suffering from diseases characterized by excessive breakdown of connective tissue.

Table 6 shows the proportions of N-Pyd and N-Dpd as a percentage of the total crosslink measured after hydrolysis in the different patient groups.

TABLE 6

| Patient Group | % N-Pyd | % N-Dpd |
|---|---|---|
| Normal controls | 43.8 ± 2.5 | 50.1 ± 5.4 |
| Osteoporosis | 41.7 ± 2.0 | 42.7 ± 2.6 |
| Paget's Disease | 46.5 ± 2.4 | 47.4 ± 4.1 |
| Hyperparathyroidism | 48.7 ± 6.8 | 46.2 ± 6.9 |
| Rheumatoid arthritis | 38.1 ± 2.6 | 43.3 ± 1.8 |
| Osteoarthritis | 43.4 ± 3.9 | 47.0 ± 2.2 |

Since, as shown in Table 6, the percentage of N-Pyd and N-Dpd is relatively unchanged in patients with abnormal conditions as compared to controls, concentrations of the N-Pyd in urine reflect the same increase in collagen degradation in diseases compared with the controls as do the total H-Pyd measured after hydrolysis of the urine.

Thus, both N-Pyd (which is effectively measured in the assay employing the monoclonal reagent, and can be calculated from the assay using polyclonal antibody reagent), pyridinium crosslinks which largely exclude Pyd-peptides greater than 1,000 molecular weight (which is measured in the assay employing a polyclonal antibody reagent), and total H-Pyd (which can be calculated from assays using either antibody reagent) are all reliable indicators of changes in bone metabolic activity associated with a variety of disease states.

The polyclonal antibodies of the invention are useful in a method for determining, in a non-hydrolyzed urine sample, a concentration of pyridinoline crosslinks that correlates with the concentration of pyridinoline crosslinks measurable after hydrolysis of the sample, with an R value of greater than 0.85, preferably greater than 0.90, and most preferably greater than 0.95. As already discussed with respect to FIGS. 1A and 1B, the I-3 polyclonal reagent correlates highly with total pyridinium crosslinks in the same sample, with a slope of about 1 and a correlation coefficient (R value) of 0.987. The high value for the slope may be due to cross-reactivity of the antibodies with small (<1000 MW) pyridinoline-peptide species. Similarly, the VI-8 polyclonal antibody reagent correlates highly, with a slope of about 0.5 and a correlation coefficient (R value) of 0.99.

Thus, the polyclonal antibodies provide a convenient means for reliably determining crosslink levels in urine, avoiding the sample hydrolysis step that has been employed in the past in measuring total pyridinium crosslink levels.

Figure 4:
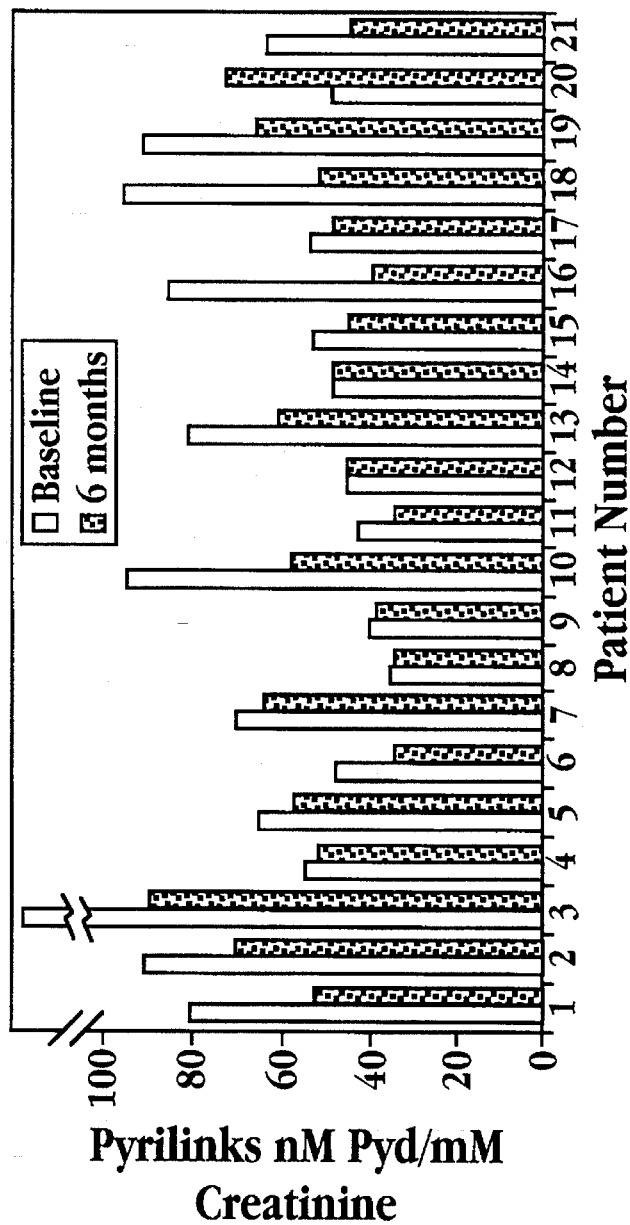
FIG. 4 shows native free pyridinoline levels measured in surgically induced menopausal women before and after 6 months of treatment with "ESTRADERM" as measured using an assay method in accordance with the invention.
Figure 5:
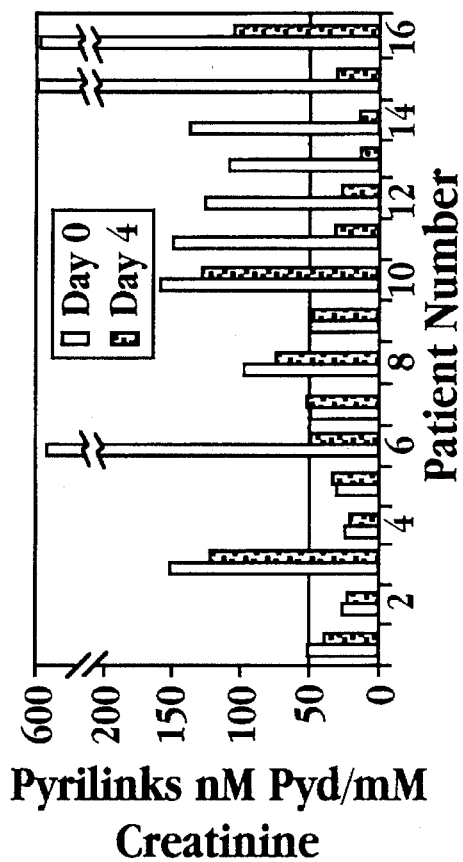
FIG. 5 shows native free pyridinoline levels measured in Paget's patients before and after 4 days of treatment with diphosphonate using the same assay method as used in FIG. 4.

Further illustrations of the usefulness of the invention are provided in FIGS. 4 and 5. FIG. 4 compares N-Pyd levels measured in urine samples from a group of 21 surgically induced menopausal women before and after 6 months of treatment with "ESTRADERM" Ciba Geigy. Native crosslinks were measured using the immunoassay format described in Example 5 with anti-Pyd polyclonal antibodies designated I-3 (Example 3C). The numbers above the bars represent the percent loss or gain from baseline values. The FIG. 4 data show that the levels of measured crosslinks fell by at least 15% in about 30% of the test group, and by over 30% in another 30% of the test group, consistent with a reduction in the rate of collagen breakdown induced by the drug.

FIG. 5 shows native free pyridinoline levels measured in urine samples from a group of 16 Paget's patients before and after 4 days of treatment with diphosphonate, as measured using the same immunoassay as for FIG. 4. The data show that in 7 patients, dramatic reductions in N-Pyd levels were observed (patient numbers 6 and 11–16), indicating that the diphosphonate treatment was particularly effective in those patients.

The data in FIGS. 4 and 5 thus show how measurement of native crosslink levels in accordance with the invention can be used to monitor the effects of treatment methods for collagen and bone-degradation conditions. Such measurements can be used to help guide the development of more effective therapeutic regimens, and to indicate which patients should benefit most from anti-resorptive therapy.

From the foregoing, it can be appreciated how the objects of the invention are met. The assay employs a non-hydrolysed urine sample, and thus avoids the need for initial sample treatment by acid hydrolysis. The assay utilizes an antibody reagent, and can thus be adapted to a number of convenient and rapid assay formats, such as the ones described above. Finally, the assay method provides an accurate quantitative measure of urinary pyridinium crosslinks from which N-Pyd and total H-Pyd can be calculated, for monitoring a variety of bone-pathology states.

The following examples illustrate methods of producing antibody reagents and assay methods, in accordance with the invention. The examples are intended to illustrate, but in no way limit, the scope of the invention.

EXAMPLE 1

HPLC Measurement of Crosslinks

HPLC analysis for Pyd and Dpd was done essentially as described in (Black, 1988). Briefly, urine samples were adjusted with butanol and glacial acetic acid to 4:1:1 (v:v:v) mixture and applied onto CF1 cellulose (Whatman) cartridge, followed by a wash with 4:1:1 (butanol:acetic acid:water) solution. Only free crosslinks were retained. The free crosslinks were eluted from CF1 cellulose with water. Eluted material was analyzed on a C18 reverse phase column (Rainin, C18-80-200-C3) using a water-acetonitrile (3–17% in 10 minutes) gradient delivered at 1 ml/minute and monitoring fluorescence at 295 nm of excitation, 395 nm of emission. Mobile phase contained 0.1% HFBA.

Total urinary crosslinks were measured by hydrolyzing a urine sample in HCl (6N) at 110° C. for 16 hours, followed by the CF1 pretreatment and HPLC analysis as above. HPLC separation yielded hydrolysed Pyd and Dpd fractions, from which T-Pyd and T-Dpd were quantitated.

EXAMPLE 2

Purification of crosslinks

Human urine was filtered through 3000 D molecular cut off filter (Filton Co.) applying 40 psi of back pressure. The filtrate was then lyophilized and reconstituted to 1/20 of the original volume with 0.2M acetic acid.

Concentrated urine was then applied onto Sephadex G-10 2.6×95 cm column equilibrated with 0.2M acetic acid. Elution from the column material was analyzed for free Pyd and Dpd as described above. The free crosslink containing fractions were pooled together, adjusted to pH 2.0 and applied onto 1×18 cm cation exchange column (Lacarte Co., UK) and equilibrated with 0.1M sodium citrate pH 4.2.

Glyco-Pyd, Pyd and Dpd were coeluted thereafter from the ion exchange column with 0.1M sodium citrate pH 4.2. Collected fractions were analyzed for the presence of crosslinks by HPLC analysis as above. Fractions containing specific crosslinks (glyco-Pyd, Pyd and Dpd) were pooled together and applied onto 2.5×10 cm reverse phase C18 column (Waters) which was subsequently developed with 2–20% gradient of acetonitrile containing 0.1% HFBA. Separated fractions (glyco-Pyd, Pyd and Dpd) were collected and concentrated by lyophilization. Dry residue was reconstituted in 0.2M acetic acid and stored at 4° C. Purity of the final material was measured by gravimetric and elementary analysis.

Urinary crosslink-peptides were prepared by exhaustive dialysis of human urine using 3500 D or 1000 D molecular weight cut off dialysis membranes (SpectraPor). The T-Pyd and T-Dpd crosslink content of the peptide fractions was determined by hydrolyzing peptide samples with 6N HCl at 110° C. for 16 hours followed by HPLC analysis for Pyd and Dpd.

Preparative amounts of H-Pyd and H-Dpd were obtained from hydrolyzed powdered bovine or sheep bone as described by Black et al. (1988).

EXAMPLE 3

Preparation of Anti-Pyridinoline Antiserum
A. Pyd-BSA Immunogen

To a 3.1 ml solution consisting of 9 mg of bovine serum albumin (BSA) and 3.8 mg of H-Pyd in 0.1M MES pH 5.0 was added an 0.88 ml aqueous solution containing 88 mg of EDC. The mixture was reacted for four hours at room temperature and was then exhaustively dialysed versus phosphate buffered saline pH 7.0 (PBS). UV and fluorescence measurements indicated 5.8 moles of pyridinoline substituted per mole of albumin.
B. Pyd-KLH Immunogen To a solution of dried H-Pyd (6 mg) in water adjusted to pH 5±0.5 (200 µl) was added 2 ml of a 10 mg/ml solution of keyhole limpet hemocyanin (KLH) in PBS. To the mixture was added 30 mg solid 1-(3-dimethylamino-propyl)-3-ethylcarbodiimide (EDC, Pierce), and ten minutes later, another 30 mg of EDC, and the reaction was allowed to proceed for 4 h at room temperature. The reaction mixture was then exhaustively dialyzed versus PBS, after which the Pyd-KLH immunogen was collected and stored.
C. Polyclonal Antibodies New Zealand white rabbits (a total of 59) for immunization were divided into eight groups according to immunization protocol, as indicated below in Table 7. The immunization dose was 200 µg of Pyd-BSA (Example 3A), low-hapten Pyd-BSA immunogen (prepared as in Example 3A for Pyd-BSA, but with a lower Pyd:BSA stoichiometry), or Pyd-KLH (Example 3B), in 1.0 ml PBS mixed with 1.0 ml of Ribi adjuvant (Ribi ImmunoChemical Research, Inc.). Initial immunization was by subcutaneous injections at multiple sites, and subsequent booster immunizations were given at three week intervals intramuscularly. Antiserum was collected 10 days after each immunization.

TABLE 7

| Program # | # of Rabbits | # Rabbits Kept | Carrier |
|---|---|---|---|
| I | 4 | 1 | BSA |
| II | 10 | 0 | BSA |
| III | 10 | 2 | BSA |
| IV | 5 | 1 | BSA |
| V | 5 | 2 | BSA |
| VI | 10 | 1 | KLH |
| VII | 5 | 0 | Low Hapten BSA |
| VIII | 10 | 1 | BSA |
| TOTALS | 59 | 8 | |

Upon collection, each antiserum was tested for Pyd binding affinity using the assay format described in Example 6. In brief, binding of anti-Pyd antibodies from the serum to Pyd immobilized on a solid support was detected using an alkaline phosphatase-labeled goat anti-rabbit IgG antibody reagent.

Immunized animals were kept if their antisera satisfied the following criteria, defined further in the following paragraph: AA<20%, Pyd-peptide<10%, titer >5000, and a 0 to 25 nM Pyd signal separation of >10% of total modulated signal.

Profiles of the most strongly reactive antisera are shown in Table 8 below, as measured using the assay format described in Example 6. The first column indicates the immunization program from which the rabbit antiserum came. The second column indicates the bleeds which were pooled for analysis. The column marked "titer" indicates the dilution of each antiserum necessary to achieve an optical density reading of 1.2 to 1.6 with a Pyd-negative sample (no Pyd present) in the immunoassay. The column marked "AA" shows the cross-reactivity of each antiserum with the amino acid mixture described in Example 7. The column marked "Pyd-pep>1000 MW" shows the cross-reactivity of each antiserum with Pyd-peptides (>1000 MW). The last column shows the separation between signals for 0 and 25 nM Pyd samples as a fraction of the total modulated signal.

TABLE 8

| Rabbit # | Bleeds | Titer | AA | Pyd-pep. >1000 MW | Sens. 25 nM |
|---|---|---|---|---|---|
| I-3 | 21–28 | 200K[1] | 2% | 4.6% | 18% |
| III-3 | 11–18 | 20K | 16% | 8.3% | 37% |
| III-5 | 11–18 | 52K | 1% | 8.1% | 13% |
| IV-4 | 4–14 | 84K | 4% | 4.9% | 10% |
| V-3 | 4–14 | 22K | 18% | 4.0% | 15% |
| V-4 | 11–14 | 9700 | 15% | 5.2% | 29% |
| VI-8 | 2–11 | 30K | 10% | 0.6% | 61% |
| VIII-4 | 3–10 | 34K | ~0% | 3.4% | 11% |

[1]K = x 1000.

As can be seen, rabbits III-3, V-4, and VI-8 showed significant modulation of signal from 0 to 25 nM N-Pyd.

The sera designated I-3 and VI-8 was selected for use in the N-Pyd assays described herein.

EXAMPLE 4

Preparation of Pyridinoline Coated Microplates

Biotin labeled ovalbumin and a streptavidin-Pyd conjugate are utilized in the microplate coating. Biotinylation of ovalbumin was carried out by adding 10 mg of biotin-X-2, 4-dinitrophenol-X-L-lysine, succinimidyl ester (Molecular Probes) in 400 microliters of dimethylformamide to a 10 ml solution of PBS containing 150 mg of ovalbumin. The mixture reacted for two hours at room temperature followed by G25 column chromatography. Spectrophotometric analysis indicated two biotins substituted per mole of ovalbumin.

The first step in conjugating N-Pyd to streptavidin was the thiolation of streptavidin with N-succinimidyl-3-(2-pyridylthio)proprionate (SPDP, Pierce). To a 0.75 ml solution of 5 mg of streptavidin in PBS was added 21 uL of dimethylformamide containing 260 ug of SPDP. The mixture was reacted for one hour at room temperature, then dialysed against PBS. The SPDP labeled streptavidin was reduced by the addition of dithiothreitol to a final concentration of 10 mM. After an incubation for one hour at room temperature, the thiolated streptavidin was purified on a G25 column. To a mixture of 0.5 mg thiolated streptavidin and 50 ug of N-Pyd in 0.10 ml of PBS was added 180 ug of succinimidyl 4-(N-maleimidomethyl)cyclohexane-1-carboxylate (SMCC, Pierce) in 4 ul of dimethylformamide. The mixture reacted for 3 hours at room temperature and was dialysed versus PBS. Spectrophotometric analysis indicated between 1 to 2 pyridinolines incorporated per mole of streptavidin.

Each of the wells in a 96-well ELISA plate were coated with N-Pyd as follows. To each well was added 150 microliters of biotin-ovalbumin solution at 3.8 ug/ml in PBS to each well followed by an overnight incubation at 2°–8° C. The microplates were washed with PBS and blocked by adding 200 ul of ovalbumin at 1 mg/ml with an overnight incubation at room temperature. The microplates are then twice washed with PBS. The streptavidin-Pyd conjugate is immobilized via the streptavidin mediated binding to biotin. 150 ul of a solution containing streptavidin-Pyd at 100 ug/ml in PBS was added to each well of the biotin-ovalbumin coated microplate. After a one hour incubation at room temperature, the plates are twice washed with PBS. Residual liquid was removed from the microplate by drying overnight in a convection oven at 37° C.

EXAMPLE 5

Immunoassay Using Polyclonal Antibody Reagent

A. Assay Method

A total of 44 urine samples from post-menopausal women were obtained from Inserm (Lyon, France). Each sample (400 μl) was filtered through a 25 mm diameter nitrocellulose filter, as described in Example 9.

96 wells of a microtitre ELISA plate were coated with Biotin-ovalbumin, and streptavidin-N-Pyd as above. 10 ul/well of 0 nM, 25 nM, 75 nM, 250 nM, 750 nM, and 3000 nM N-Pyd standard solutions were added in duplicate to 12 of the 96 wells in the coated plates and SMCC ELISA plate and 10 ul/well of each of the 44 urine samples were added in duplicate to the wells of two microtitre plates.

Sample addition to the wells was followed by 150 uL of the anti-Pyd polyclonal serum from Example 3 (I-3 antibodies), at a final dilution of 1:45,000 in PBS with 1 mg/ml of BSA and 0.05% Tween 20. The plates were incubated for overnight at 2°–8° C. then washed three times with 300 uL of PBS. 150 μl of a goat anti-rabbit IgG alkaline phosphatase conjugate (American Qualex) at a final dilution of 1:2000 in PBS, 1 mg/mL BSA 0.05, Tween 20 is dispensed to each well.

After an incubation of one hour at room temperature, the plates were washed three times with 300 uL of PBS. 150 uL of the enzyme substrate, 2 mg/mL of p-nitro-phenylphosphate (Sigma) in 1.0M diethanolamine 1 mM MgCl$_2$ pH 9.8, was added. Following a one-hour incubation at room temperature, 50 μl of 3.0N NaOH is added to each well to stop the enzymatic reaction. The optical density at 405 nm was then measured with a Vmax reader (Molecular Devices Corp.).

B. Assay Results

The optical density readings (405 nm) from each duplicate sample were averaged, and the average readings from the six Pyd standards were used to construct a standard curve of Pyd concentration vs. OD reading. From this curve, the pyridinium crosslink concentrations from each of the 44 urine samples was determined. Pyridinium crosslink concentration values ranged from very low levels (less than 50 nM) to greater than 1,000 nM.

The same urine samples were quantitated for total Pyd by the HPLC method described in Example 2. Briefly, the urine samples were hydrolysed in HCl (6N) at 110° C. for 16 hours, followed by the CF1 pretreatment and HPLC analysis for total H-Pyd.

FIG. 1 shows a scatter plot of pyridinium crosslinks (in nM) measured by the immunoassay method (y axis) measured vs. total H-Pyd measured by HPLC. The line in the plot is the best-fit linear regression equation which correlates immunoassay values as a function of HPLC total Pyd values.

EXAMPLE 6

Binding Selectivity of Polyclonal Antibody reagent

N-Pyd, N-Dpd, glyco-Pyd, Pyd-peptide (MW>1000, and Pyd-Peptide (MW>3500) were isolated from urine samples as described above. Aliquots of the glyco-Pyd and two Pyd-peptide preparations were hydrolysed to convert the crosslinks in the fractions to H-Pyd. Aliquots of the pyridinium preparations were hydrolysed to convert the crosslinks in the fractions to H-Pyd and H-Dpd. The concentrations of Pyd in the N-Pyd and H-Pyd preparations, of Dpd in the N-Dpd and H-Dpd preparations, and of Pyd in the pyridinium-peptide preparation, were determined by HPLC, as in Example 1. In addition, an amino acid solution containing an equimolar mixture of the 20 common amino acids, 150 μM each in PBS, was prepared.

Aliquots (50 μ) of the native crosslink preparations and the amino acid mixture were added in duplicate to Pyd-coated microtitre wells, and each well was assayed for pyridinoline as in Example 5. The optical density readings (405 nm) from duplicate samples were averaged, and from these values, the apparent N-Pyd concentration of each sample was determined using a standard curve established with purified N-Pyd. The percent reactivity of each sample was calculated as a ratio of apparent concentration (measured using the N-Pyd standard curve above) to total Pyd crosslink concentration in the sample determined by HPLC for total H-Pyd (times 100). The relative reactivity determined for purified N-Pyd was arbitrarily set at 100%, and the reactivities of the other crosslink preparations (and the amino acid mixture) were expressed as a percentage of 100. Results obtained with this assay are shown in Tables 1 and 2 above.

EXAMPLE 7

Immunoassay Using Monoclonal Antibody Reagent

Monoclonal antibodies were obtained from hybridoma cell line identified ATCC No. HB11089. The cells were grown in Dulbecco's modified Eagle's medium (DMEM) under standard conditions. The antibody obtained from the cells is designated Mab H-Pyd XXV-3G6-3B11-1A10.

96 wells of a microtitre ELISA plate were coated with Biotin-ovalbumin, and streptavidin-N-Pyd as above. Twenty ul/well of 0 nM, 25 nM, 75 nM, 250 nM, 750 nM, and 3000 nM N-Pyd standard solutions (Example 5) were added in duplicate to 12 of the 96 wells in the coated plates and 20 ul/well of each of the 44 filtered urine samples (Example 5) were added in duplicate to wells of two microplates.

100 ul/well of MAb 3G6-3B11-1A10 (1:100,000 dilution) in assay buffer (0.05% NAN3, 0.05% Tween 20, and 0.1% BSA in PBS) were added into Elisa plate. The standards or samples and MAb mixtures were incubated at 4° C. overnight. 100 μl/well of second antibodies goat anti-mouse IgG+M(H+L)-alkaline phosphatase conjugate (Pierce, No. 31330) (1:1000 dilution in assay buffer) were added to ELISA plate, and incubated at room temperature for one hour. Bound enzyme was assayed as in Example 5. The pyridinium crosslink concentration for each unknown urine sample was determined by quantitation from the standard curve.

FIG. 2 shows a scatter plot of pyridinium crosslinks (in nM) measured by the immunoassay method (y axis) measured vs. total H-Pyd measured by HPLC (as in Example 5). The line in the plot is the best-fit linear regression equation which correlates immunoassay values as a function of HPLC total Pyd values.

EXAMPLE 8

Binding Selectivity of Monoclonal Antibody Reagent

N-Pyd, N-Dpd, H-Pyd, H-Dpd, Pyd-peptides (MW>1000), and Pyd-peptides (MW>3500) were isolated from urine samples as described above. Aliquots of the two Pyd-peptide preparations were hydrolysed to convert the crosslinks in the fractions to H-Pyd. The concentration of Pyd in the N-Pyd and H-Pyd preparations, and in the two Pyd-peptide preparations, and concentrations of Dpd in N-Dpd and H-Dpd preparations were determined by HPLC, as in Example 1.

Aliquots (20 μl) of the five crosslink preparations were added in duplicate to microtitre wells prepared as in Example 4, and each well was assayed for pyridinium crosslinks as in Example 5. The optical density readings (405 nm) from each duplicate sample were averaged, and from these values, relative concentrations of pyridinium crosslinks in the samples which are immunoreactive with the antibody reagent were determined. The concentration determined for the N-Pyd sample was arbitrarily set at 100%, and the concentrations of the other five preparations were expressed as a percentage of 100. The results are given in Table 3 above.

EXAMPLE 9

Sample Pretreatment By Nitrocellulose Filtration

Six urine samples, designated 2181, 2176, 2159, 2167, 2161, and 2172 were tested. Aliquots (400 μl) of each sample was filtered through a 25 mm diameter nitrocellulose filter (Millipore, Millex-HA, Bedford, Mass.) and the filtrate was collected in a tube.

Aliquots (10 μl) of filtered and unfiltered sample material and N-Pyd standards were added in duplicate to the wells of a 96 well ELISA plate prepared as above, and the concentrations of pyridinium crosslinks in each sample was determined as above, using a polyclonal antibody reagent. The results are given in Table 4 above.

EXAMPLE 10

Correlation Between N-Pyd and T-Pyd in Urine

A. Isolation of N-Pyd and N-Dpd

Urine samples were collected from patients with Paget's disease or hyperparathyroidism (which contain elevated levels of free crosslinks) and from growing children (in which about 10-fold higher concentrations of crosslinks are present compared with normal adults). After concentration 10-fold by rotary evaporation, batches of the urine (20 liters) were subjected to partition chromatography batchwise on cellulose CF1 using butanol:acetic acid:water (4:1:1 v/v/v) as mobile phase. The pyridinium crosslink-containing fraction, eluted from the stationary phase with water, was chromatographed on a column (3.2×150 cm) of Sephadex G-10 eluted with 0.2M acetic acid.

Pooled fractions containing the crosslinks were then made 67 mM in $Na^+$ and applied to a column (1.7×35 cm) of Dowex 50X-X8 ion-exchange resin equilibrated with 67 mM sodium citrate buffer, pH 2.75. After raising the column temperature to 60° C. elution with 67 mM sodium citrate was performed with a linear pH gradient from 2.75 to 5.05 over 500 ml. The column effluent was monitored by fluorescence (ex 325 nm/em 400 nm) and the pooled fractions containing N-Pyd (364–377 ml) and N-Dpd (397–416 ml) were desalted by gel filtration on Sephadex G-10 and evaporated to dryness. The yield from 20 liters of urine was 2.5 μmoles N-Pyd and 0.6 μmoles N-Dpd.

B. Results

The isolation procedure set forth in paragraph A sample was applied to urine samples from individual patients and the amounts of N-Pyd and N-Dpd were quantitated using fluorescence measurements of HPLC-isolated material relative to creatinine (Cook, et al.). The values obtained for normal individuals and in 7 patients with bone disorders and arthritic diseases are shown in Table 5 above. Values are given as the mean±SEM (n=6 in each group).

Total H-Pyd was determined from an aliquot of each of the samples, after hydrolysis, as described in Example 2. The percentages of N-Pyd and N-Dpd in the sample, calculated as N-Pyd/Total-Pyd×100 and N-Dpd/Total-Pyd×100, are given in Table 6. Urinary creatinine was determined by published methods.

Although the invention has been described with respect to particular embodiments, it will be appreciated that various changes and modifications can be made without departing from the invention.

It is claimed:

1. A method of determining a concentration of pyridinoline crosslinks in a non-hydrolyzed urine sample, comprising obtaining a non-hydrolysed urine sample from a human subject, reacting the sample with a polyclonal antibody reagent produced by immunizing an animal with hydrolyzed pyridinoline conjugated to a carrier, by said reacting, forming an immunocomplex between pyridinoline crosslinks in the urine sample and the antibody reagent, and detecting the amount of immunocomplex formed.

2. The method of claim 1, which further includes, prior to said reacting, passing the urine sample through a nitrocellulose filter.

3. The method of claim 1, wherein said reacting includes contacting the urine sample with a solid-phase support having surface-attached pyridinoline molecules effective to compete with pyridinoline crosslinks in the sample for binding to the antibody reagent.

4. The method of claim 1, wherein the antibody reagent is attached to the surface of a solid-support, and said reacting is conducted in the presence of a reporter-labeled pyridinoline reagent effective to compete with pyridinoline crosslinks in the sample for binding to the antibody reagent.

5. The method of claim 1, wherein the antibody reagent has a binding constant, measured with respect to native free pyridinoline, of greater than $1\times10^7$/molar.

* * * * *